Figure 1:
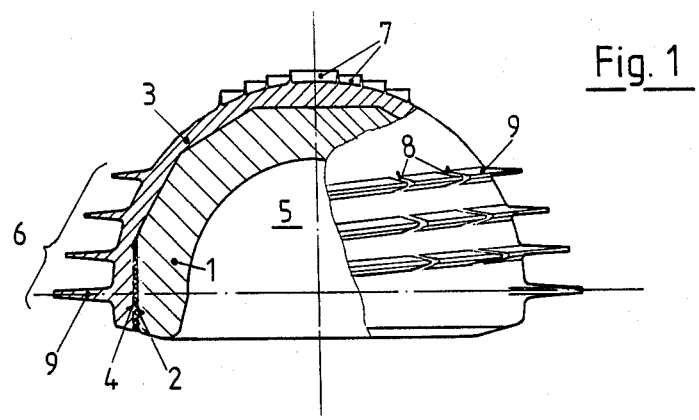

United States Patent [19]

Stuhmer

[11] Patent Number: 4,822,367

[45] Date of Patent: Apr. 18, 1989

[54] ENDOPROSTHESIS FOR A HIP JOINT SOCKET

[75] Inventor: Karl-Gerhart Stuhmer, Ravensburg, Fed. Rep. of Germany

[73] Assignee: Sulzer Brothers Limited, Winterthur, Switzerland

[21] Appl. No.: 11,070

[22] Filed: Feb. 4, 1987

[30] Foreign Application Priority Data

Feb. 18, 1986 [CH] Switzerland .......................... 651/86

[51] Int. Cl.$^4$ .............................................. A61F 2/34
[52] U.S. Cl. ........................................ 623/22; 623/18
[58] Field of Search ....................... 623/16, 19, 20, 21, 623/22, 23

[56] References Cited

FOREIGN PATENT DOCUMENTS

| 0065482 | 11/1982 | European Pat. Off. | ............. | 623/22 |
| 0190981 | 8/1986 | European Pat. Off. | ............. | 623/22 |
| 3446048 | 10/1985 | Fed. Rep. of Germany | ....... | 623/22 |
| 82/02555 | 8/1983 | PCT Int'l Appl. | .................... | 623/22 |
| 86/02261 | 4/1986 | PCT Int'l Appl. | .................... | 623/22 |
| 1222265 | 4/1986 | U.S.S.R. | ............................... | 623/22 |

OTHER PUBLICATIONS

ROM 135 "Total Hip Prosthesis" Joint Med. Proc. Corp. 1983.

Primary Examiner—Richard J. Apley
Assistant Examiner—David J. Isabella
Attorney, Agent, or Firm—Kenyon & Kenyon

[57] ABSTRACT

The endoprosthesis for a hip joint socket is provided with a plastic socket body, a metallic outer shell and a screw thread on the surface of the shell. The screw thread has a constant pitch with each turn of the screw thread having a length (L) of from 4 to 12 millimeters, a base width of from 0.15L to 0.2L and a crest width of from 0.025L to 0.05L.

11 Claims, 1 Drawing Sheet

U.S. Patent  Apr. 18, 1989  4,822,367

ENDOPROSTHESIS FOR A HIP JOINT SOCKET

This invention relates to an endoprosthesis for a hip joint socket. More particularly, this invention relates to an endoprosthesis for a hip joint socket for cement-free anchoring in a pelvis.

As is known, various types of endoprosthesis have been used to form a hip joint socket for anchoring in the pelvis of a human body. In some cases, the endoprostheses have been constructed for a cement-free anchoring in the pelvis. For example, European Patent EP-A-0144588 describes an endoprosthesis having a hemispherical outer shell made of pure titanium or a titanium alloy and a plastic socket body fixed within the outer shell. In addition, the outer surface of the outer shell is provided with a screw thread of constant pitch with the turns of the screw thread divided by notches which extend in meridian lines of the shell. With such prostheses, the socket bodies are made predominantly of plastic, for example polyethylene, since such offers good sliding properties. However, the outer shells are generally made of a body-compatible metal such as pure titanium for reasons of strength.

However, a problem generally exists with the above type of prosthesis in that the elasticity of the outer shell differs greatly from that of the pelvis. Thus, while the threaded outer shell is capable of supporting bearing loads in the direction of the axis of rotation of the prosthesis, bending moments which are exerted on the prosthesis, for example from a joint head, generally formed by a prosthesis as well, are not efficiently transmitted to the pelvis.

Accordingly, it is an object of the invention to improve the mounting of an endoprosthesis for a hip joint socket in a pelvis.

It is another object of the invention to impart an elasticity to an endoprosthesis for a hip joint socket without unduly impairing the strength of the endoprosthesis and without inducing undesirable plastic deformation.

It is another object of the invention to improve on the transmission of bending forces through an endoprosthesis for a hip joint socket to a pelvis.

Briefly, the invention provides an endoprosthesis for a hip joint socket having a plastic socket body, a metallic outer shell receiving the socket body and having a hemispherical outer surface and a screw thread on the surface of the shell of constant pitch. In addition, the screw thread has a plurality of turns with each turn having a length (L) of from 4 millimeters to 12 millimeters, a base width of from 0.15 L to 0.2 L and a crest width of from 0.025 L to 0.05 L.

Where the socket body has been made of polyethylene and the outer shell of pure titanium, it has been found on the basis of tests that the above noted relationships for the dimensions of the turns of the screw thread offer assurance for optimum fulfillment of the requirements of strength in the shell and elasticity in the thread which are, at least in part, contradictory to each other.

The endoprosthesis construction also provides additional advantages in that a relatively large bearing and support surface in the direction of the axis of the endoprosthesis is provided and in that good transmission of the bending moments exerted from a joint head onto the bone is provided. The transmission of the bending moments and, in general, the adhesion of the endoprosthesis in a pelvis, can be improved by providing annular cutting edges in a polar region of the outer shell.

In addition, the screw thread can be sub-divided by spaced apart notches which are disposed along meridian lines of the shell.

Figure 2:
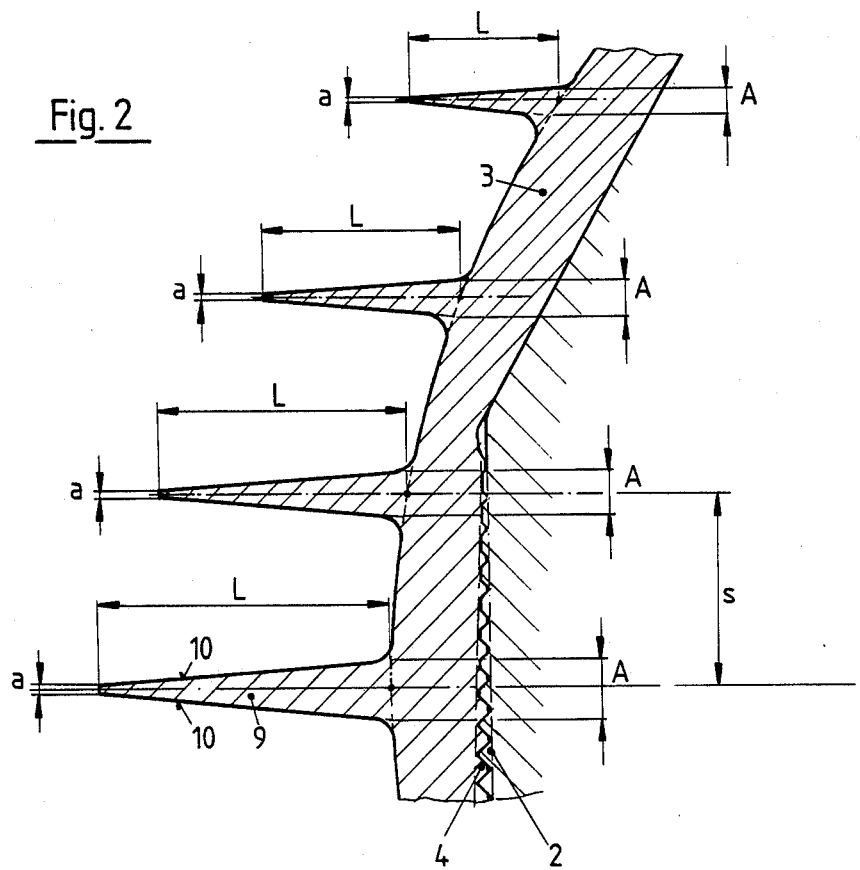

These and other objects and advantages of the invention will become more apparent from the following detailed description taken in conjunction with the accompanying drawings wherein:

FIG. 1 illustrates a partial view of an endoprosthesis constructed in accordance with the invention; and FIG. 2 illustrates a meridian sectional view of a part of the endoprosthesis of FIG. 1.

Referring to FIG. 1, the endoprosthesis is constructed for use as a hip joint socket and for implanting in a cement-free manner in a pelvis of a human body. As shown, the endoprosthesis includes a plastic socket body 1 having an outer surface which forms a semi-polygon in cross section. In addition, the outer surface of the socket body 1 is provided with a circumferential thread 2 about the flat surface which forms the equatorial side of the socket body 1.

The endoprosthesis also includes a metallic outer shell 3 which is provided with an internal thread 4 in order to threadably receive the socket body 1. A socket shell 5 in the form of a hollow hemisphere is fitted inside of the socket body 1 in order to receive a joint head of a femur head prosthesis (now shown).

The outer shell 3 is provided with a hemispherical outer surface for anchoring in a pelvis as well as with a multi-spiral screw thread 6 of constant pitch, for example 6.5 millimeters. As indicated in FIG. 1, the screw thread 6 is provided at the equator of the shell 3 and extends through the near and middle latitudes. The polar region of the shell 3 is provided with a plurality of annular cutting edges 7 in the form of circular rings. As the prosthesis is being screwed into a pelvis, the cutting edges 7 cut into the bone tissue and add to the fixation of the prosthesis. The cutting edges 7 also provide an additional abutment for any bending moments exerted by the femur head prosthesis after implantation.

Referring to FIG. 2, the screw thread 6 has a plurality of turns 9 each of which is disposed on an axis perpendicular to a common axis of rotation of the socket body 1 and the shell 5. Also, as indicated in FIG. 1, the screw thread 6 has a plurality of spaced apart notches 8 which extend along meridian lines of the shell 3 in order to sub-divide the screw thread 6. As illustrated, the length L of the screw thread decreases continuously from the equator towards the polar regions. In this respect, the length L is measured in the median plane of each turn 9 as the distance between the surface of the shell 3 and the crest of the turn 9. For outer shells 3 of titanium or titanium alloys, the length L of each turn 9 is from 4 millimeters to 12 millimeters.

Referring to FIG. 2, each turn 9 of the screw thread has a pair of flanks 10 which merge into the outer shell 3 via a fillet-type radius. The base of each turn 9 is defined by the points of intersection of the prolonged flanks 10 with the hemispherical surface of the outer shell 3. The width or thickness A of each base of a turn 9 is from 0.15L to 0.2L while the width a of a thread turn 9 at the crest lies in the range of from 0.025 L to 0.05 L.

By observing the above relationships of the length and width of the thread turns 9, an optimum ratio results between the elasticity of the thread turns 9, on the one hand, and the strength as well as the resistance to permanent information, on the other hand.

As indicated in FIGS. 1 and 2, the screw thread 6 is integral with the shell 3. For example, the screw thread 6 can be machined during manufacture of the shell 3, for example, by a numerically controlled tapping or by a mill cutting out of a solid blank.

The invention thus provides an endoprosthesis for a hip joint socket having a metallic outer shell with an integral screw thread thereon for cutting into a pelvis wherein the outer shell and thread turns are provided with as great an elasticity as possible without unduly impairing the strength properties of the shell and without inducing undesirable plastic, i.e. permanent, deformation.

What is claimed is:

1. An endoprosthesis for a hip joint socket having a metallic hemispherical outer shell having an equator and a polor region and a screw thread on said shell having a constant pitch and spaced apart notches therein extending along meridian lines of said shell, said screw thread being of decreasing length from the equator towards the polar region of said shell and having a plurality of turns with each turn having a length (L) of from 4 millimeters to 12 millimeters, a base width (A) of from 0.15L to 0.2L and a crest width (a) of from 0.025L to 0.05 L.

2. An endoprosthesis as set forth in claim 1 wherein said shell has a plurality of annular cutting edges in a polar region thereof.

3. An endoprosthesis as set forth in claim 1 wherein said pitch is 6.5 millimeters.

4. An endoprosthesis as set forth in claim 1 wherein said shell and said thread are made of a material selected from the group consisting of titanium and titanium alloy.

5. An endoprosthesis as set forth in claim 1 further having a plastic socket body threaded into said shell.

6. An endoprosthesis for a hip joint socket comprising
a plastic socket body;
a metallic outer shell receiving said socket body therein and having a hemispherical outer surface having an equator and polar region; and
a screw thread on said surface of said shell, said screw thread being of decreasing length from the equator towards the polar region of said shell and having a constant pitch and a plurality of turns with each turn having a length (L) of from 4 millimeters to 12 millimeters, a base width (A) of from 0.15 L to 0.2 L and a crest width (a) of from 0.025 L to 0.05 L.

7. An endoprosthesis as set forth in claim 6 wherein said thread has spaced apart notches therein to subdivide said thread.

8. An endoprosthesis as set forth in claim 7 wherein said notches are disposed along meridian lines of said shell.

9. An endoprosthesis as set forth in claim 6 wherein said shell has a plurality of annular cutting edges in a polar region thereof.

10. An endoprosthesis as set forth in claim 6 wherein said shell and said thread are made of a material selected from the group consisting of titanium and titanium alloy.

11. An endoprosthesis as set forth in claim 6 wherein each said turn is disposed on an axis perpendicular to a common axis of rotation of said body and said shell.

* * * * *

UNITED STATES PATENT AND TRADEMARK OFFICE
CERTIFICATE OF CORRECTION

PATENT NO. : 4,822,367

DATED : April 18, 1989

INVENTOR(S) : Karl-Gerhart Stuhmer

It is certified that error appears in the above-identified patent and that said Letters Patent is hereby corrected as shown below:

Column 3, line 2 "information" should be -deformation-

Signed and Sealed this

Sixth Day of February, 1990

*Attest:*

JEFFREY M. SAMUELS

*Attesting Officer*    *Acting Commissioner of Patents and Trademarks*